United States Patent [19]

Hill et al.

[11] Patent Number: 4,546,766

[45] Date of Patent: Oct. 15, 1985

[54] THERAPEUTIC TRACTION APPLIANCE HAVING SELF-CALIBRATING MECHANISM

[75] Inventors: Howard A. Hill, Malvern; James A. Sack, Downingtown, both of Pa.

[73] Assignee: Hill Laboratories, Inc., Malvern, Pa.

[21] Appl. No.: 585,542

[22] Filed: Mar. 2, 1984

[51] Int. Cl.[4] .......................... A61F 5/01; F16D 65/52

[52] U.S. Cl. ...................................... 128/71; 188/71.8

[58] Field of Search ........................ 128/71, 51, 52, 57, 128/62 R, 33, 34; 188/71.8

[56] References Cited

U.S. PATENT DOCUMENTS 2,822,805 2/1958 Hill ........................................ 128/71

3,550,728 12/1970 Seip et al. .......................... 188/71.8

*Primary Examiner*—Richard J. Apley

*Assistant Examiner*—Alan W. Cannon

*Attorney, Agent, or Firm*—Howson and Howson

[57] ABSTRACT

A device for applying a controlled amount of traction to a human body. The device includes an arm one end of which is connected by a harness to a patient for applying traction periodically as the patient pivots the arm and the other end of which is connected by a ratchet assembly to a drag wheel rotatably mounted in a frame. The magnitude of the traction applied is determined by the amount of friction applied to the wheel by a pair of opposed brake pads engaging opposite sides of the wheel. A manual adjusting mechanism is provided for one of the brake pads to set a desired level of traction to be applied by the arm, and a calibrating mechanism is connected to the other brake pad for automatically adjusting the same during operation of the manual adjusting mechanism.

9 Claims, 5 Drawing Figures

THERAPEUTIC TRACTION APPLIANCE HAVING SELF-CALIBRATING MECHANISM

FIELD OF THE INVENTION

The present invention relates to therapeutic appliances, and more particularly, the present invention relates to appliances for use in applying a controlled amount of traction to a human body.

BACKGROUND OF THE INVENTION

U.S. Pat. No. 3,830,233, owned by the assignee of the present application, discloses a therapeutic device which is designed to apply periodically a controlled amount of traction to a human body. The device includes a table having a top which reciprocates lengthwise to move a patient lengthwise in the course of treatment. A traction applicator unit mounted at one end of the table has an arm which projects upwardly and which is adapted to be coupled at its upper end to a harness connected to the patient lying on the table. The arm is connected to a brake drum by a ratchet mechanism which causes the brake drum to rotate unidirectionally each time the arm is pivoted as the table moves the patient away from the traction unit. The magnitude of the traction applied to the patient is controlled by a brake shoe which surrounds the drum and which is connected to an adjustment mechanism.

U.S. Pat. No. 2,882,805 and U.S. Pat. No. 2,781,040, both owned by the assignee of the present application, also disclose therapeutic tables of similar construction.

While the aforementioned patented treatment tables function satisfactorily for their intended purposes, there is a need for certain improvements. For instance, while the traction adjusting mechanism is calibrated at the factory prior to shipment, the user must frequently calibrate the mechanism in order to insure the application of an accurate amount of traction to the patient. This is due to the tendency of the brake shoe to wear over a period of time. Brake shoe wear induces error in the traction adjustment settings. To maintain accuracy in the adjustment settings, the unit is calibrated by connecting a spring scale to the arm and pulling on the scale to pivot the arm and thereby to measure the tension applied for a given setting of the adjustment mechanism. Thereafter, appropriate notations are made on the scale of the adjustment mechanism to correct for the error induced as a result of brake shoe wear. Needless to say, this procedure is time consuming and, therefore, undesirable.

OBJECTS OF THE INVENTION

With the foregoing in mind, a primary object of the present invention is to provide an improved therapeutic appliance for use in applying an accurately controlled amount of traction to a human body without requiring periodic calibration.

Another object of the present invention is to provide a unique therapeutic appliance which has a self-calibrating mechanism enabling the appliance to apply accurate amounts of traction to a patient.

A still further object of the present invention is to provide a novel self-calibrating traction unit which is particularly suited for use in combination with a therapeutic table having a reciprocating top for periodically applying accurately controlled amounts of traction to a patient positioned thereon.

SUMMARY OF THE INVENTION

More specifically, the present invention provides an appliance for enabling an accurately controlled amount of traction to be applied to a patient. The appliance includes a frame, a drag wheel rotatably mounted in the frame, and an arm adapted to be connected at one end to the patient for applying traction and operatively connected adjacent its other end to the drag wheel by a ratchet mechanism which rotates the drag wheel when the arm is pivoted. A means is provided for applying friction to the drag wheel to adjust the magnitude of the tension applied by the arm to the patient as the patient is displaced relative to the appliance. The friction applying means includes a pair of brake pads engaging opposite sides of the wheel. One brake pad is connected to a manual adjusting mechanism, and the other brake pad is connected to a calibrating mechanism which cooperates with the adjusting mechanism to automatically displace the pad against the wheel to compensate for wear of both brake pads each time the adjusting mechanism is cycled.

BRIEF DESCRIPTION OF THE DRAWINGS

The foregoing and other objects, features and advantages of the present invention should become apparent from the following description when taken in conjunction with the accompanying drawings, in which.

DESCRIPTION OF THE PREFERRED EMBODIMENT

Figure 1:
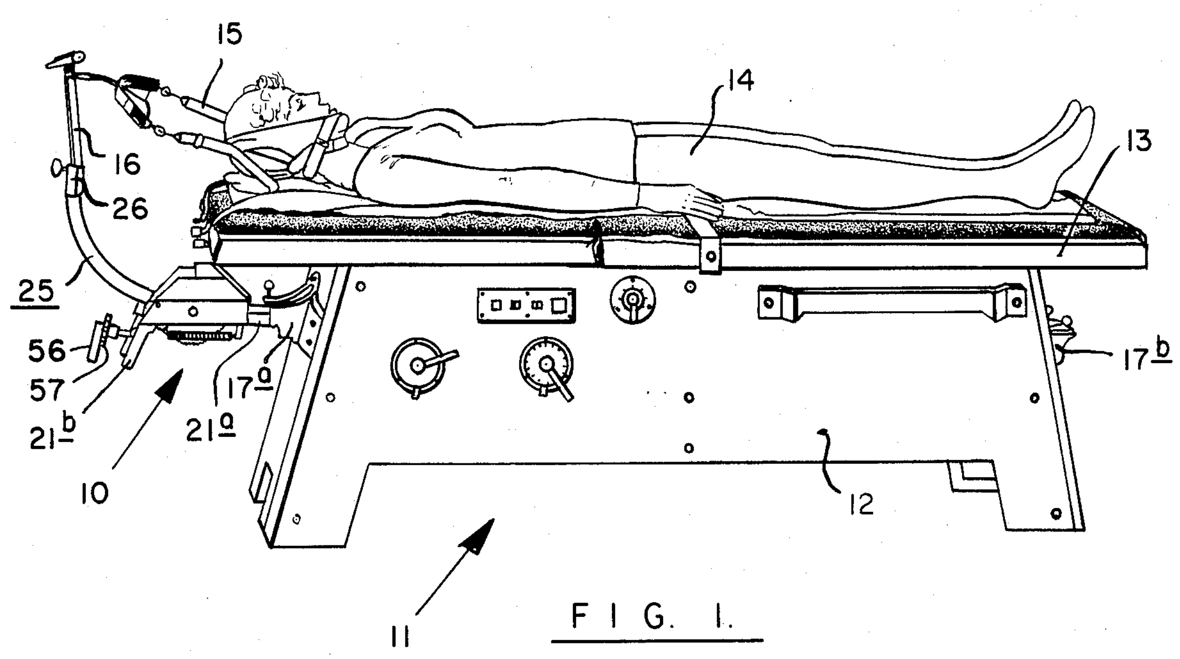
FIG. 1 is a perspective view of a therapeutic table having a traction appliance embodying the present invention mounted at its left end.

Referring now to the drawings, FIG. 1 illustrates a traction appliance 10 which embodies the present invention. The appliance 10 is shown mounted at the left-hand end of a treatment table 11 of the type described in U.S. Pat. No. 3,830,233, the disclosure of which is incorporated by reference herein. As described in that patent, the treatment table 11 includes a base 12 and a top 13 which is reciprocated back and forth in the direction indicated by the arrow by a mechanism contained within the base 12. In the illustrated embodiment, cervical traction is applied to a patient 14 lying on the table top 13 through a halter assembly 15 which is connected to the traction appliance 10 by an arm extension 16. With this apparatus, displacement of the treatment table top 13 in the rightward direction on the advance portion of its stroke causes the patient 14 to move rightward. This, in turn, causes the halter 15 to pull on the arm extension 16 for pivoting the same clockwise while the traction appliance 10 connected thereto simultaneously applies tension in the leftward direction to the halter 15. As the table top 13 moves leftward on its return stroke, return springs pivot the arm extension 16 counterclockwise to maintain tension on the halter 15 but at a lower level than applied during the advance portion of the table stroke.

In FIG. 1, the patient 14 is shown undergoing cervical traction. Lumbar traction can also be applied simply by disconnecting the traction unit 10 from the bracket 17*a* located at the left hand end of the table base 12 and installing it in the bracket 17*b* located at the right hand end of the table base 12. The traction assembly 10 is then connected by means of a suitable harness arrangement to the patient's feet.

As discussed above, traction units used heretofore in combination with the table 11 were less than entirely satisfactory because of their need to be calibrated periodically in order to ensure that an accurate amount of traction is applied to the patient. Periodic calibration was necessitated by the proclivity of the brake shoe in the traction unit to wear over the course of time. Calibration is a time consuming task and must be performed carefully to ensure accuracy.

According to the present invention, the traction assembly 10 is designed to eliminate the need for periodic calibration so that it is capable of applying accurately controlled amounts of traction to a patient. To this end, the traction unit 10 comprises a frame 20 which includes a pair of L-shaped frame members 21 and 22 having inner ends 21*a* and 22*a* adapted to be inserted in the bracket 17*a* in the manner illustrated in FIG. 1. The frame members 21 and 22 have downturned outer ends 21*b* and 22*b* (FIG. 2) connected together by a transverse strut 23. The frame members 21 and 22 are similarly connected adjacent their inner ends by a transverse strut 24.

Figure 2:
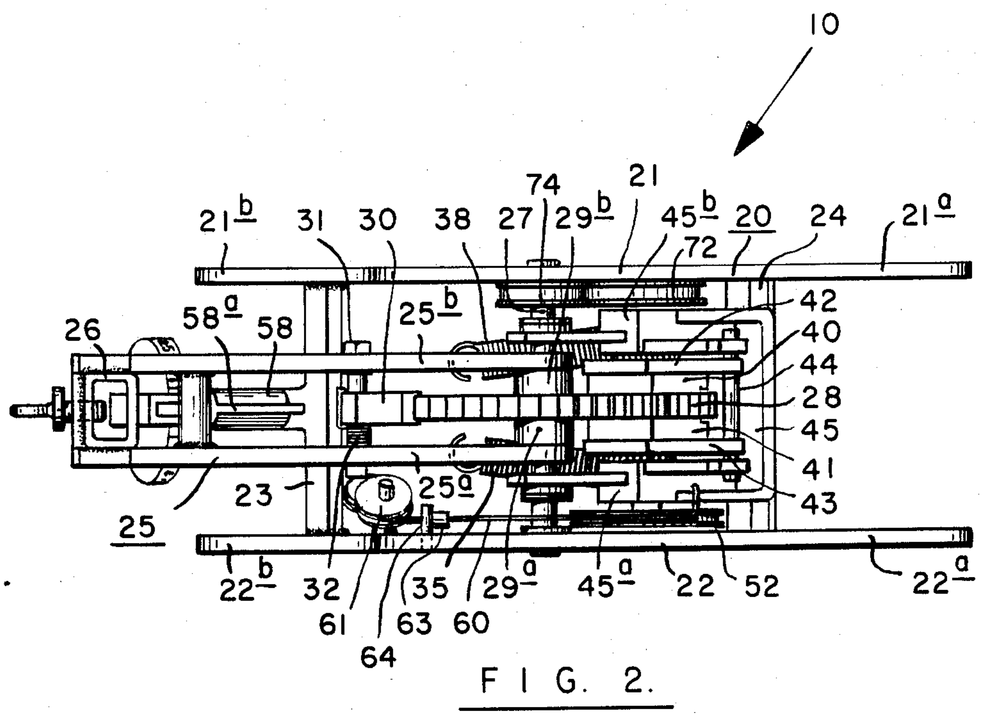
FIG. 2 is an enlarged plan view of the traction appliance with its protective cover removed.
Figure 3:
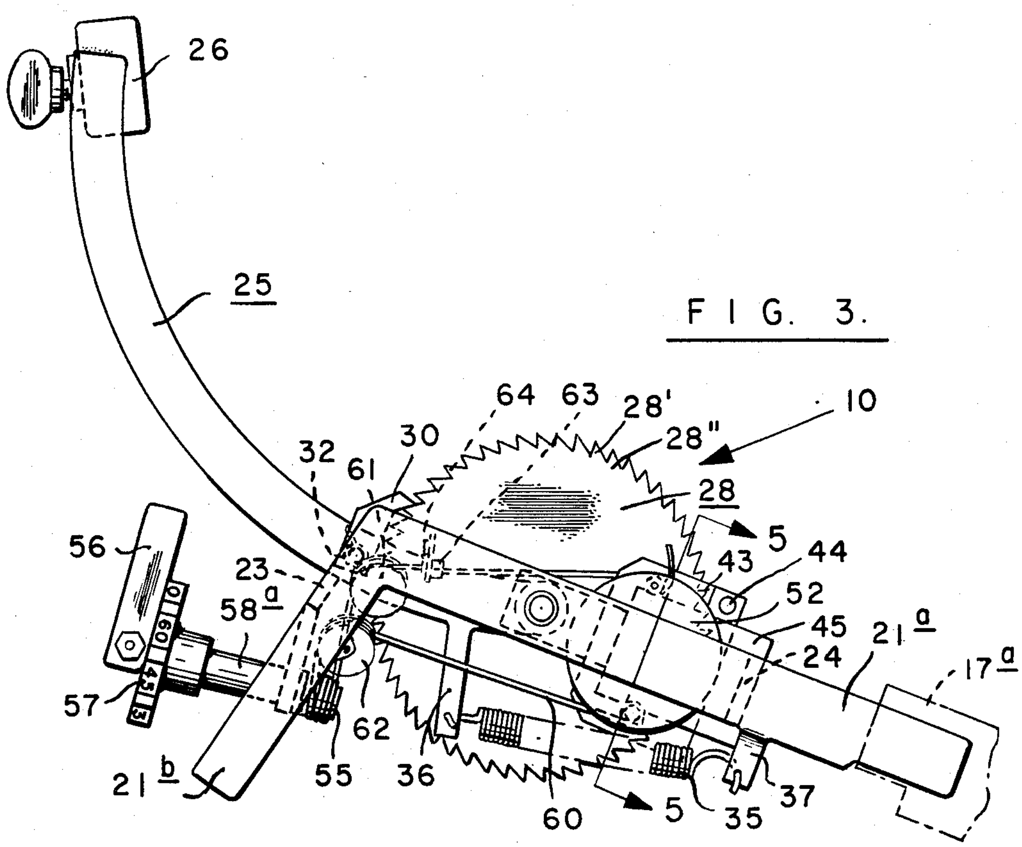
FIG. 3 is an enlarged side elevational view of the traction appliance illustrated in FIG. 2.

As best seen in FIGS. 1 and 3, the traction unit 10 includes an arcuate arm 25 which projects upwardly from the frame 20 and which mounts at its upper end a clamping assembly 26 adapted to slidably receive the arm extension 16 which is connected to the halter 15. As best seen in FIG. 2, the arm 25 includes a pair of curved bars 25*a* and 25*b* extending in spaced parallel relation and pivotally mounted adjacent their lower ends to a shaft 27 extending transversely across the frame members 21 and 22. The arm members 25*a* and 25*b* straddle a rotary drag means which, in the illustrated embodiment, includes a flat wheel 28 mounted to rotate on the shaft 27 and to slide axially thereon a slight distance as determined by the bushings 29*a* and 29*b* interposed between the arm members 25*a* and 25*b* and the wheel 28.

The arm 25 is connected to the drag wheel 28 by means of a ratchet assembly which rotates the wheel unidirectionally each time the arm pivots. For this purpose, and as best seen in FIG. 3, a series of teeth 28' are provided about the outer periphery of the wheel 28 for cooperating with a pawl 30 mounted between the arm members 25*a* and 25*b* on a bolt 31. The pawl 30 is biased into engagement with the teeth 28' on the wheel 28 by means of a torsion spring 32. As a result, pivotal movement of the arm 25 clockwise (FIG. 3) causes the wheel 28 to rotate clockwise about its shaft 27 by virtue of the interengagement of the pawl 30 with the teeth on the periphery of the wheel 28.

The arm 25 is biased into its home position illustrated in full lines in FIG. 3 to maintain a minimum tension on the halter 15 of about five pounds during the return stroke of the table top 13. To this end, a pair of extension springs 35 and 38 extend underneath the frame 20 to connect the arm 25 to the frame 20. The springs, such as the spring 35, are connected between spurs on the arm members, such as the spur 36 which depends from the arm member 25*a* and ears on the frame members, such as the ear 37 depending from the frame member 22 adjacent its inner end 22*a*. Counterclockwise pivotal movement of the arm 25 by the springs 35 and 38 is limited by the engagement of the arm 25 with the frame strut 23. Thus, the arm 25 is normally disposed in the position illustrated in FIG. 1 when the table top 13 is in its leftwardmost limit position at the beginning of the traction applying cycle.

In order to apply to the halter 15 a controlled amount of substantially constant tension greater than the amount pivoted provided by the return springs 35 and 38, as the patient 14 moves rightward with the table top 13, friction, or drag, is applied to the wheel 28. In the present invention, as best seen in FIG. 2, the friction is applied by a pair of brake shoes, or pads, 40 and 41 opposed to one another and engaging opposite sides of the wheel 28 adjacent its periphery. The brake pads are secured to mounting plates 42 and 43, respectively, which are slidably mounted on a pin 44 which in turn is mounted on a pair of trunnions projecting upwardly from a U-shaped caliper block 45 mounted in the frame 20 adjacent the periphery of the wheel 28.

For purposes to be described, a means is provided to mount the caliper block 45 for sliding movement in the frame 20 relative to the wheel 28. To this end, the caliper block 45 is provided with a groove in the side opposite the wheel 28. The groove slidably engages the transverse frame strut 24 to support the caliper block at one end, and the caliper block 45 has a pair of stub arms 45*a* and 45*b* which extend along opposite sides of the wheel 28 and which are slidably mounted on the shaft 27 to slidably support the other end of the caliper block 45. See FIG. 2. Thus, the brake pads 40 and 41 are mounted in the caliper block 45 for movement toward and away from the sides of the wheel 28, and the caliper block 45 is mounted for movement relative to the wheel 28.

For the purpose of adjusting the amount of traction applied to the patient 14, a means is provided on the frame 20 for adjusting the friction, or drag on the wheel 28. In the present invention, this is achieved by adjusting the pressure applied by the brake pads 40 and 41 to the wheel 28. To this end, a first means is provided to couple the brake pad 41 to the caliper block arm 45*a* in a manner permitting movement of the brake pad 41 toward and away from the wheel 28. In the illustrated embodiment, the first coupling means includes a boss 50 which loosely engages the brake pad plate 43 and which is fastened to the inboard end of a threaded rod 51 threadedly received in the caliper block arm 45*a*. A pulley 52 is mounted on the outboard end of the threaded rod 51 and functions, when rotated, to turn the threaded rod 51 for displacing the boss 50 either inward or outward either to increase the pressure or to relieve the pressure, as described. Thus, pressure applied by the brake pad 41 to the wheel 28 can be adjusted simply by rotating the pulley 52.

In order to enable the pulley 52 to be rotated from a convenient location with respect to the table 11, a flexible actuator assembly is provided. In the illustrated embodiment, the flexible actuator assembly includes a capstan 55 mounted in a bearing 58 between the frame members 21*b* and 22*b* for rotation on an axis aligned with the path of movement of the wheel 28. The capstan 55 is rotated by means of a handle 56 provided on an adjusting wheel 57. The adjusting wheel 57 has indications imprinted thereon which function, when aligned with a pointer 58*a* on the capstan bearing 58 (FIG. 2) to provide an indication as to the magnitude of traction applied to the patient 14. The capstan 55 is connected to the brake pad pulley 52 by a cable 60 which is wrapped in opposite directions about the brake pad pulley 52 and the capstan 55. A pair of idler pulleys 61 and 62 are mounted in the frame 22 for guiding the cable 60 as it changes direction while passing between the capstan 55 and brake pad pulley 52.

In order to permit the indicator wheel 57 to be reset readily to the minimum traction condition, a means is provided to limit the travel of the cable 60. For this purpose, a stop 63 is swaged onto the cable 60 for cooperating with an eye 64 mounted to the frame member 22*a* to limit the travel of the cable 60. The location of the stop 63 on the cable 60 is determined by the minimum position of the indicator wheel 57 with respect to the pointer 58 and is preset at the factory prior to shipment. Thus, rotation of the indicator wheel 57 by its handle 56 in the clockwise direction (looking rightward in FIG. 1) causes the pulley 52 to rotate clockwise (FIG. 3) for displacing the brake shoe 41 into engagement with the wheel 28 and increasing pressure and hence friction thereon. Rotation of the indicator wheel 57 in the opposite direction disengages the boss 50 from the brake pad plate 43 and allows the brake pad 41 to move rightward away from the wheel 28 for reducing the amount of pressure and hence friction applied thereby to the wheel 28.

The pressure applied by the manually-adjusted brake pad 41 to obtain the wheel 28 is counterbalanced by pressure applied in the opposite direction by its companion automatically-adjusted brake pad 40 by virtue of the slidable mounting of the caliper block 45 on its mounting strut 24 and the shaft 27. For example, motion of the brake pad 41 leftward (FIG. 5) in engagement with the right side of the wheel 28 causes a reaction force in the caliper block 45 to displace the caliper block 45 rightward for urging the companion brake pad 40 into reactive engagement with the left side of the wheel 28. Thus, substantial amounts of pressure can be applied to the wheel 28 between the brake pads 40 and 41 without inducing bending stresses on the wheel 28 and/or other stresses in the shaft 27.

Figure 4:
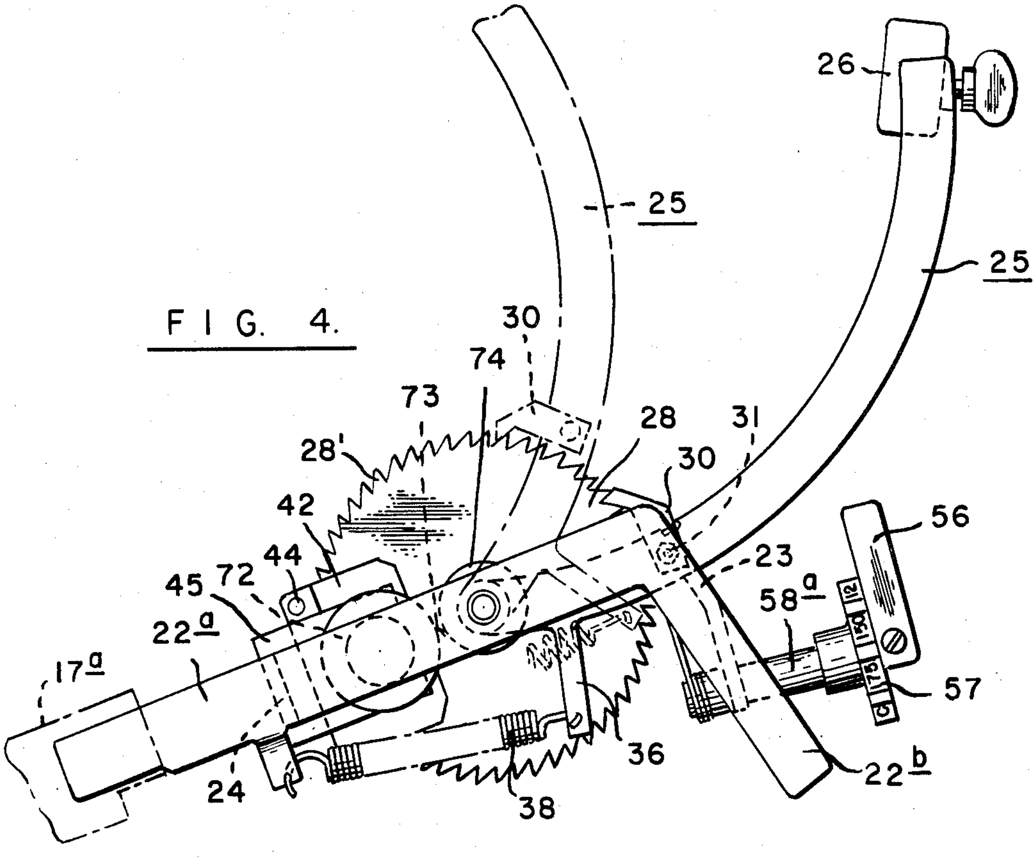
FIG. 4 is a side elevational view of the traction appliance illustrating the side opposite the side illustrated in FIG. 3.
Figure 5:
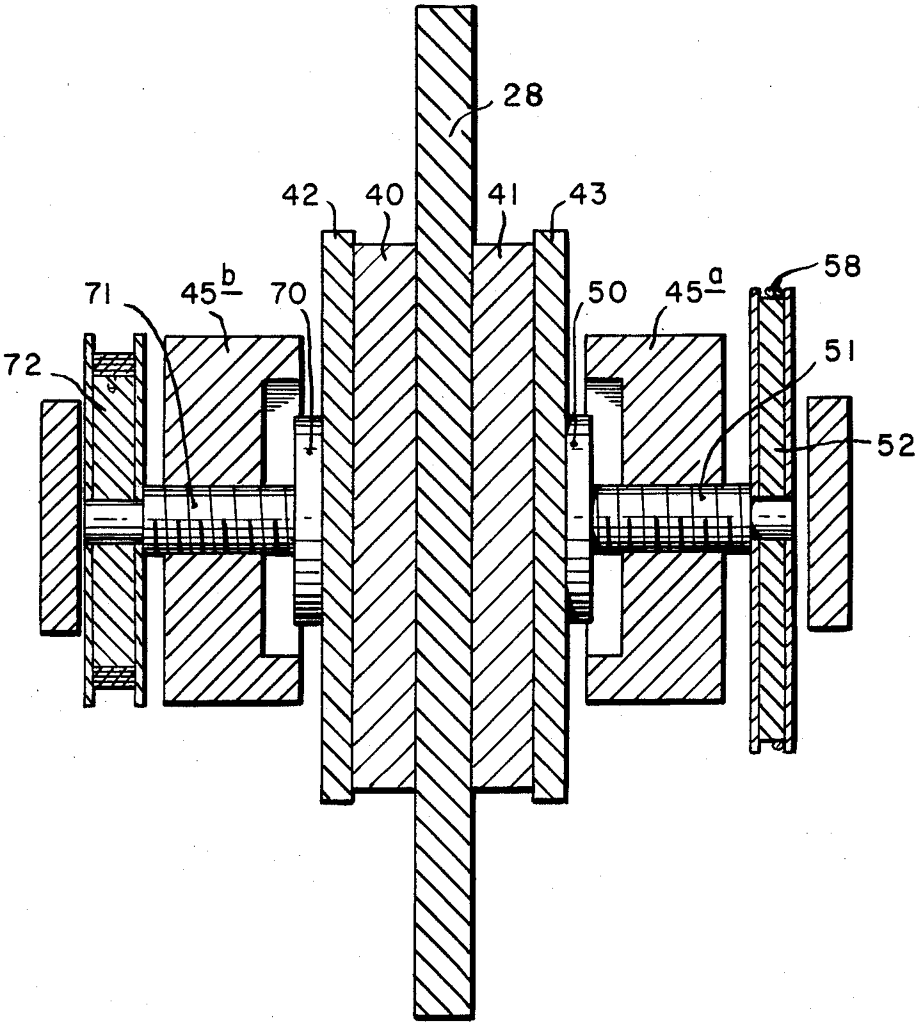
FIG. 5 is a greatly enlarged sectional view taken on line 5—5 of FIG. 3.

According to the present invention, the traction unit 10 calibrates itself automatically each time the manual adjusting mechanism coupled to the brake pad 41 is cycled to its minimum traction level. To this end, the automatically-adjusted brake pad 40 is biased into engagement with its side of the wheel 28, and by virtue of the slidable mounting of the caliper block 45 in the frame 20, the manually-adjusted brake pad 41 is thereby biased into engagement with its side of the wheel 28. In the present instance, the brake pad 40 is mounted in the caliper block 45 in a manner similar to the manner in which the brake pad 41 is mounted. Thus, as best seen in FIG. 5, a boss 70 is mounted on the inboard end of a threaded rod 71 which is threadedly received in the arm 45*b* of the caliper block 45. The outboard end of the threaded rod 71 is connected to a spring motor which functions to bias the boss 70 into engagement with the brake pad plate 42 for continuously urging the brake pad 40 against the wheel 28 and displacing the caliper block 45 leftward (FIG. 5). The spring motor comprises a driven drum 72 mounted on the outboard end of the threaded rod 71 and connected by a band of spring steel 73 to a storage drum 74 mounted on the shaft 27. The spring band 73 cooperates with the storage drum 74 in a well known manner to rotate the same counterclockwise (FIG. 4) for normally rotating the driven drum 72 clockwise. Clockwise pivotal movement of the driven drum 72 turns the threaded rod 71 to urge the brake pad 40 rightward (FIG. 5). As the brake pad 40 moves rightward it displaces the caliper block 45 leftward. This causes the opposing brake pad 41 to move leftward. Thus, the brake pad 40 is always maintained in engagement with the wheel 28 under a pressure determined by the force exerted by the spring motor connected thereto. In turn, the wheel 28 is always maintained in engagement with the opposing brake pad 41 as a result of the slidable mounting of the caliper block 45 on the frame strut 24 and the wheel mounting shaft 27.

In using the traction unit 10 of the present invention, the adjusting wheel 57 is rotated toward its minimum setting prior to being set at a desired level of traction. As the minimum level is reached, the automatically-adjustable brake pad 40 is displaced rightward as a result of the biasing action of the spring motor, and the manually-adjusted brake pad 41 moves leftward into engagement with the wheel 28 due to the sliding motion of the caliper block 45 on its mounting strut 24. Thereafter, when the adjustment wheel 57 is rotated in the opposite direction away from its minimum setting to set the desired level of traction to be applied to the patient 14, pressure on the manually-adjusted brake pad 41 increases. However, by virtue of the previous action of the spring motor, the brake pad 40 is displaced a slight distance rightward to compensate for whatever pad wear may have occurred so that, when pressure is again applied to wheel 28 by the brake pad 41, such pressure is opposed by the reaction thereagainst of the companion brake pad 40. Leftward movement of the manually-adjusted brake pad 41 and the caliper block 45 causes the pulley 52 to move leftward; however, such motion is accommodated by the ability of the cable 60 to shift through an angle in the horizontal plane between the idlers 61 and 62 and the pulley 52. Thus, the traction unit 10 automatically compensates for any brake pad wear which may have occurred the last time the table was used so that the operator can be assured that the amount of traction set by the indicator wheel 57 corresponds accurately with the amount of traction applied to the patient.

In view of the foregoing, it should be apparent that the present invention has now provided a traction unit which is capable of applying accurately a controlled amount of traction to a patient. Since the traction unit 10 calibrates itself automatically each time the unit is manually adjusted into its minimum position, it should be apparent that the traction unit 10 operates in a manner which ensures the application of accurately controlled amounts of traction to a patient without requiring periodic manual calibration now required by prior art traction units. The traction unit 10 is designed to apply traction in a range of 5 lb. to 200 lb., 5 lb. being the minimum amount applied when the adjustment wheel is set at its minimum setting. The traction unit 10, constructed as illustrated, has been found capable of applying traction smoothly throughout the full range of movement of the arm. The unit 10 is also relatively light in weight but very durable. While the traction device 10 is particularly suited for purposes of applying periodic traction in combination with a table having a reciprocating top, it can also be utilized to exercise arm and leg muscles simply by providing a suitable grip between a patient's arm or leg and the traction unit 10.

While a preferred embodiment of the present invention has been described in detail, various modifications, alterations and changes may be made without departing from the spirit and scope of the present invention as defined in the appended claims.

We claim:

1. In a device for applying a controlled amount of tension to a human body, including frame means, rotary means mounted in said frame means, an arm pivotally mounted in the frame means and adapted to be connected to the human body for applying said tension thereto, means on said arm and rotary means cooperable to rotate said rotary means in response to alternating pivotal movement of said arm, brake means for applying friction to said rotary means, and adjustable means coupled to said brake means for adjusting the magnitude of the friction applied by said brake means, the improvement wherein said brake means includes a pair of brake pads mounted in opposed relation on opposite sides of said rotary means for movement in a path along its rotational axis, caliper block means slidably mounted in said frame adjacent to the periphery of said rotary means for mounting said brake pads, first means coupling one of said brake pads to said caliper block for movement relative thereto, and second means coupling the other of said brake pads to said caliper block for movement relative thereto, calibrating means connected to said second coupling means for normally urging said one brake pad toward said rotary means, and adjusting means connected to said first coupling means for selectively displacing said one brake pad toward and away from said rotary means, said calibrating means being operable automatically when said one brake pad is displaced away from said rotary means to cause said other brake pad to move toward said rotary means and upon engagement therewith to displace said calibrating block relative to said rotary means and to urge said one brake pad toward said rotary means.

2. Apparatus according to claim 1 wherein said first and second brake pad coupling means includes first and second screw means threaded into said caliper block with said second screw means being operable upon rotation to displace its brake pad relative to said caliper block and to displace said caliper block with respect to said rotary means.

3. Apparatus according to claim 2 wherein said calibrating means includes elastic means connected to said second screw means for rotating the same to displace the brake pad connected thereto against said rotary means in response to axial movement of said one brake pad away from said rotary means in the course of actuation of said adjusting means.

4. Apparatus according to claim 3 wherein said elastic means includes a constant force spring motor connected to said second screw means for normally rotating the same in one direction to bias said other brake pad against said rotary means.

5. Apparatus according to claim 4 wherein said spring motor includes a driven drum connected to said second screw means, a driving drum aligned with said driven drum, and a spring band interconnecting the peripheries of said drums to cause said driving drum to rotate said driven drum in said one direction.

6. Apparatus according to claim 2 wherein said one brake pad adjusting means includes a pulley connected to said first screw means, a capstan rotatably mounted in said frame, and a cable wrapped in opposite directions around the periphery of said pulley and said capstan, whereby rotation of the capstan in one direction causes said one brake pad to move toward the rotary means to increase friction thereon and rotation of the capstan in the opposite direction causes said one brake pad to move away from the rotary means to decrease friction thereon.

7. Apparatus according to claim 6 including a handle connected to said capstan for rotating the same, means mounting said capstan in said frame for rotation about an axis at an angle to the path of movement of the rotary means, and idler pulleys mounted in said frame for guiding said cable between said pulley and said capstan.

8. Apparatus for use in applying a controlled amount of tension to a human body, comprising a frame, an arm having one end pivotally mounted in said frame and having another end adapted to be coupled to the body, a wheel rotatably mounted in said frame, means between said wheel and arm cooperable upon pivotal movement of said arm in opposite directions between a home position and an extended position to rotate said wheel, first and second opposed brake pads engaging opposite sides of said wheel, adjustable means in said frame mounting said first brake pad for movement toward and away from said wheel, calibrating means in said frame mounting said second brake pad for biased movement toward said wheel automatically in response to movement of said first brake pad away from said wheel in the course of operation of said adjustable means, and means connecting said calibrating and adjusting means together so that movement of said second brake pad toward said wheel causes said first brake pad to move toward said wheel.

9. Apparatus for use in applying a controlled amount of tension to a human body, comprising: a frame, a wheel mounted for rotary motion in said frame, an arm pivotally mounted in said frame and having one end adapted to be coupled to said body, means connecting said arm to said wheel for causing said wheel to rotate in response to pivotal movement of said arm, a pair of brake pads mounted in opposed relation on opposite sides of said wheel, adjustable means connected to one of said brake pads for displacing the same toward and away from said wheel, spring-powered calibrating means connected to the other of said brake pads for automatically urging the same into engagement with said wheel as said one brake pad moves away from said wheel during actuation of said adjustable means, and caliper block means slidably mounted in said frame and mounting said adjustable means and said spring powered calibrating means for shifting movement relative to said wheel when said other brake pad engages said wheel and shifts said caliper block in a direction causing said one brake pad to engage the wheel.

* * * * *